(12) United States Patent
Trusler et al.

(10) Patent No.: US 12,343,276 B2
(45) Date of Patent: Jul. 1, 2025

(54) KNEE BRACE

(71) Applicants: UNIVERSITY OF CAPE TOWN, Cape Town (ZA); Michael Stuart Barrow, Johannesburg (ZA)

(72) Inventors: Matthew Graham Trusler, Sandton (ZA); Michael Stuart Barrow, Johannesburg (ZA)

(73) Assignee: UNIVERSITY OF CAPE TOWN, Cape Town (ZA)

(*) Notice: Subject to any disclaimer, the term of this patent is extended or adjusted under 35 U.S.C. 154(b) by 468 days.

(21) Appl. No.: 17/628,152

(22) PCT Filed: Jul. 17, 2020

(86) PCT No.: PCT/IB2020/056745
§ 371 (c)(1),
(2) Date: Jan. 18, 2022

(87) PCT Pub. No.: WO2021/014309
PCT Pub. Date: Jan. 28, 2021

(65) Prior Publication Data
US 2022/0273480 A1    Sep. 1, 2022

(30) Foreign Application Priority Data

Jul. 19, 2019  (GB) ..................... 1910408

(51) Int. Cl.
*A61F 5/01* (2006.01)

(52) U.S. Cl.
CPC .... *A61F 5/0125* (2013.01); *A61F 2005/0167* (2013.01); *A61F 2005/0179* (2013.01)

(58) Field of Classification Search
CPC ............ A61F 5/0585; A61F 2005/0132; A61F 2005/0167; A61F 2005/0169;
(Continued)

(56) References Cited

U.S. PATENT DOCUMENTS 4,361,142 A * 11/1982 Lewis ................... A61F 5/0123
602/26
4,370,977 A    2/1983 Mauldin et al.
(Continued)

FOREIGN PATENT DOCUMENTS

EP        3090708 A1 * 11/2016 ........... A61F 5/0123

OTHER PUBLICATIONS

Vivian Grisogono, About the Calf, 2016.*
(Continued)

*Primary Examiner* — Alireza Nia
*Assistant Examiner* — Andrew Jun-Wai Mok
(74) *Attorney, Agent, or Firm* — Fitch, Even, Tabin & Flannery LLP

(57) ABSTRACT

A knee brace having an upper part securable about a user's thigh and a lower part securable about the user's lower leg is provided. The upper and lower parts are secured together adjacent the user's knee by a hinge. The knee brace is characterised in that a flexible tensioning element extends between the upper part and the lower part over a lobe which is secured to the upper part adjacent the hinge such that pivoting of the upper and lower parts about the hinge causes the flexible element to engage the lobe about its periphery to cause tension in the flexible element and wherein the lobe is shaped to cause the tension to dynamically increase as the upper part is pivoted relative to the lower part.

10 Claims, 10 Drawing Sheets

(58) Field of Classification Search
CPC ...... A61F 2005/0179; A61F 2005/0197; A61F 5/01–0195; B25J 9/00; B25J 9/0006
See application file for complete search history.

(56) References Cited

U.S. PATENT DOCUMENTS

| | | | |
|---|---|---|---|
| 4,433,679 A * | 2/1984 | Mauldin | A61F 5/0102 602/26 |
| 2010/0056970 A1 | 3/2010 | Nace | |
| 2011/0098618 A1 | 4/2011 | Fleming | |
| 2012/0071803 A1 | 3/2012 | Jansson | |
| 2013/0110020 A1* | 5/2013 | Ingimundarson | A61F 5/0123 602/26 |
| 2015/0119777 A1* | 4/2015 | Garrish | A61F 5/0123 602/16 |
| 2015/0374531 A1 | 12/2015 | Fedon | |
| 2019/0053933 A1 | 2/2019 | Chetlapalli et al. | |

OTHER PUBLICATIONS

Vivian Grisogono, About the Shin, 2016.*
Opahle et al., Knee Brace for Applying a Ventrally or Dorsally Directed Translatory Force, Nov. 9, 2016.*
International Search Report and Written Opinion of the International Searching Authority issued in International Patent Application No. PCT/IB2020/056745, Oct. 16, 2020, 12 pages.

* cited by examiner

KNEE BRACE

CROSS-REFERENCE TO RELATED APPLICATIONS

This application is a U.S. national phase application filed under 35 U.S.C. § 371 of International Application Number PCT/IB2020/056745, filed Jul. 17, 2020, designating the United States, which claims priority from British Application Number 1910408.2, filed Jul. 19, 2019.

FIELD OF THE INVENTION

The present disclosure relates to an orthopaedic device, more particularly, to a knee brace for supporting a knee of a subject. The knee brace may be useful for a subject recovering from a posterior cruciate ligament (PCL) injury or surgery.

BACKGROUND TO THE INVENTION

The knee joint forms the interface between the femur and tibia and is stabilised by four primary ligaments. These are the anterior cruciate ligament (ACL), the posterior cruciate ligament (PCL), the medial collateral ligament (MCL) and the lateral collateral (LCL) ligament. The ACL, which is the best known and most commonly injured of these ligaments, keeps the tibia from sliding too far forwards (in an anterior direction) with respect to the femur. Conversely, the PCL prevents the tibia from sliding too far backwards (in a posterior direction) with respect to the femur.

PCL injuries are generally sustained when the tibia is forcibly moved posteriorly with respect to the femur, such as when the knee is contacted during a fall or a motor vehicle accident. When a PCL is torn, the proximal end of the tibia tends to shift posteriorly, causing strain on the healing tendon and often causing the PCL to elongate relative to its pre-injury condition. This can result in loosening of the knee once the tear has healed such that the proximal end of the tibia is able to move posteriorly relative to the femur, causing instability and an increase in the likelihood of further injury.

A known technique for dealing with problems related to the PCL involves immobilising the knee in a partial or total plaster cast, or in a generic knee brace to provide a degree of stability. These solutions are, however, inadequate as they prevent flexing of the knee joint during rehabilitation which can limit a user's range of motion, increase discomfort and contribute to atrophy of the leg muscles.

Some knee braces can provide support to the lower leg throughout a range of motion and may be used to limit posterior shifting of the tibia and minimise elongation of the PCL during healing. However, these types of knee braces tend to be expensive and difficult to install on a user's leg, rendering them unsuited to clinical use in poorly-resourced areas. There is therefore a need for an easy to install, relatively inexpensive orthopaedic device that can be worn by a user suffering from a PCL injury which allows a degree of supported leg flexion.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of the invention, there is provided a knee brace having an upper part securable about a user's thigh and a lower part securable about the user's lower leg, the upper and lower parts secured together by a hinge, characterised in that a flexible tensioning element extends between the upper part and the lower part over a lobe which is secured to the upper part adjacent the hinge such that pivoting of the upper part relative to the lower part about the hinge causes tension in the flexible tensioning element and wherein the lobe is shaped to cause the tension to dynamically increase as the upper part is pivoted relative to the lower part.

The lobe may define an involute curved surface about its periphery for engaging the flexible element. The lobe may be releasably secured to the upper part, which may include a lobe receiving formation capable of receiving lobes of varying configurations. The lobe may be secured so that it does not rotate or move with respect to the upper part during flexion or pivoting of the upper part relative to the lower part. The lobe may include a securing formation configured to engage a complementary engaging formation on the upper part to secure the lobe in fixed orientation with respect to the upper part. The securing formation may be provided by a clip, latch, detent, tongue, groove or opening, and may be configured to engage a complementary engaging formation on the upper part to secure the lobe in position. Where the securing formation is provided by an opening, it may be configured to engage a complementary projection on the upper part.

The knee brace may further include a calf supporting member, which may be hingedly secured to an operatively lower portion of the lower part, at or about an ankle region thereof, by a pivot member. The calf supporting member may define an elongate channel and may be configured to support a region of a user's lower leg extending from the user's lower Achilles tendon region to the user's upper calf region.

The flexible tensioning element may be secured to the calf supporting member. The flexible tensioning element may be configured to urge the calf supporting member to pivot about the pivot member in an anterior direction when the flexible tensioning element is tensioned, such as during knee flexion.

The knee brace may include a further lobe such that the two lobes together provide a medial lobe and a lateral lobe, with the medial lobe secured adjacent a medial hinge and the lateral lobe secured adjacent a lateral hinge.

The brace may include a common flexible tensioning element engaging both the medial and lateral lobes. The common flexible tensioning element may be adjustable to a desired user tension. Alternatively, separate flexible tensioning elements may engage the medial lobe and the lateral lobe respectively, and each of the separate flexible tensioning elements may be independently adjustable to a desired user tension.

An embodiment of the invention will now be described, by way of example only, with reference to the accompanying drawings.

DETAILED DESCRIPTION WITH REFERENCE TO THE DRAWINGS

Figure 1:
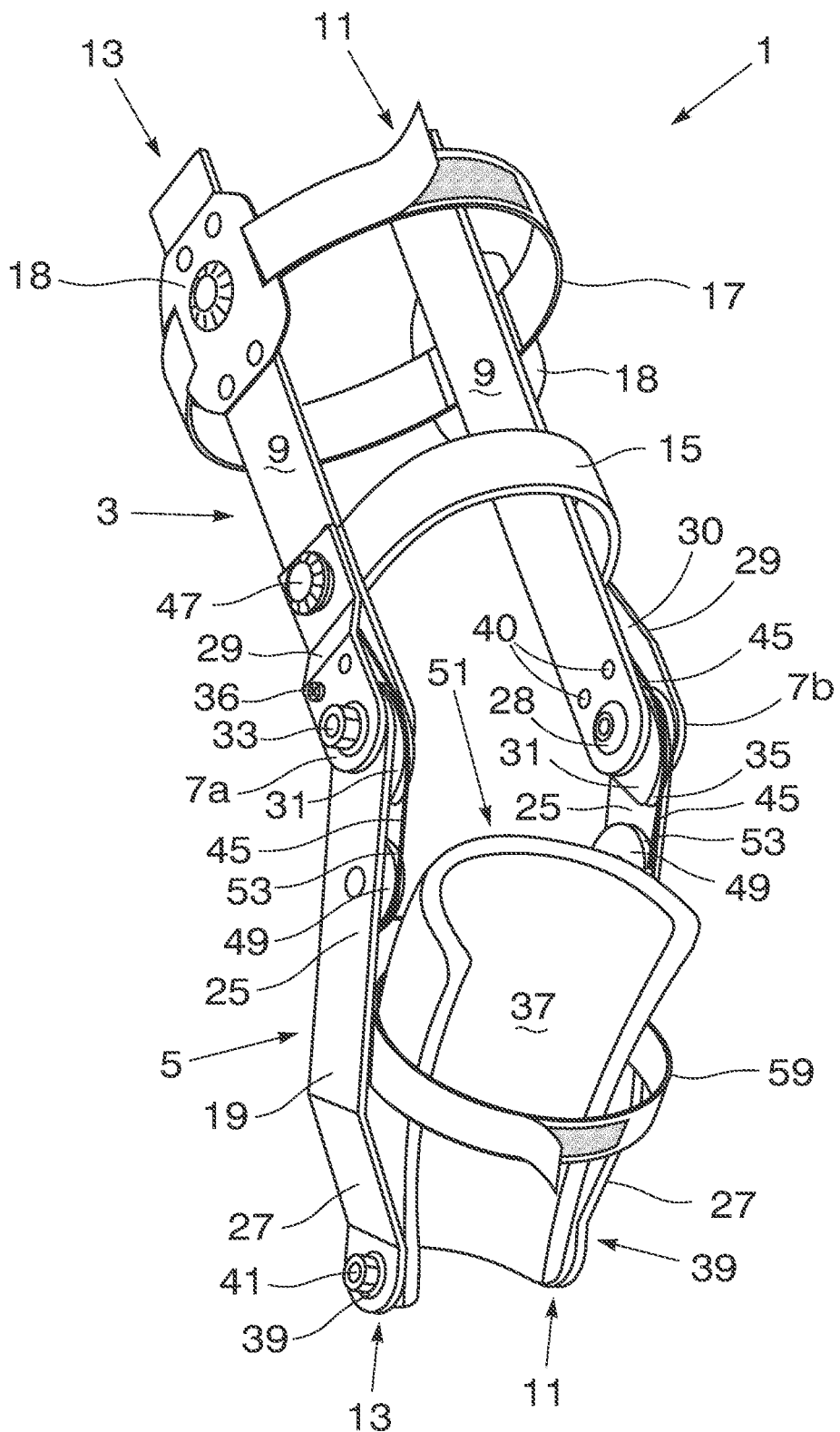
FIG. 1 is a three dimensional view of a knee brace according to the present disclosure.

The present disclosure provides a knee brace for supporting a knee of a subject recovering from a posterior cruciate ligament (PCL) injury or surgery. The knee brace is useful for limiting posterior movement of the subject's tibia relative to the subject's femur which might otherwise result in elongation of the PCL and instability in the knee once the PCL has healed.

The knee brace has an upper part securable about a user's thigh and a lower part securable about the user's lower leg. The upper and lower parts are secured together by a hinge, which may operatively be located adjacent the user's knee when the knee brace is secured to the user's leg. The knee brace further includes a flexible tensioning element that extends between the upper part and the lower part over a lobe which is secured to the upper part adjacent the hinge such that pivoting of the upper part relative to the lower part about the hinge causes tension in the flexible element. The lobe is shaped to cause the tension to dynamically increase as the upper part is pivoted relative to the lower part. A dynamic increase in tension refers to an increasing degree of tension in the flexible tensioning element with each increasing increment of flexion of the upper part relative to the lower part. The flexible tensioning element may be provided by a cable, strap, tape, cord or wire, although other suitable flexible elements may also be used.

The upper and lower parts may each be provided by a pair of substantially parallel rigid struts operatively located on lateral and medial sides of the knee brace and which engage each other about lateral and medial hinges, respectively. The struts may be formed from a rigid material, which may be a metal, wood, plastic or a composite.

The lobe may be disc-shaped and have a groove or channel in its periphery in which the flexible element is received. The periphery may be defined between two major surfaces of the lobe. A pair of lobes may be secured to each of the struts of the upper part adjacent the lateral and medial hinges, respectively. The lobe may define an involute curved surface about its periphery for engaging the flexible element. An involute curve refers to a curve defined by a path hypothetically taken by an end of an idealised string as it wraps around a curve or circle. The slope of an involute curve increases along a perimeter of the curve in one direction and decreases in an opposite direction. The curvature of the lobe increases about its periphery in a generally downward and rearward direction in use. A substantially straight section of the lobe may intersect with the curved surface to form a point, which may operatively point downwards.

The lobe may be releasably secured so that it does not rotate or move with respect to the upper part during flexion or pivoting of the upper part relative to the lower part. The lobe may be secured to a lobe receiving formation on the upper part which may be capable of receiving lobes of varying configurations. Different sized lobes may generate different rates of dynamic tension in the flexible tensioning element during flexion, with larger lobes producing greater tension than smaller lobes. The lobe receiving formation may include a releasable fastener and in some embodiments may be provided by a nut and bolt or by a quick release fitting, such as a clip or skewer, to permit a user preferred lobe to be selected and secured with relative ease. An aperture may be provided in the lobe through which the lobe receiving formation may be received. A securing formation may also be included in the lobe for securing the lobe in fixed orientation with respect to the upper part. The securing formation may be provided by a clip, latch, detent, tongue, groove, opening, or the like, and may be configured to engage a complementary engaging formation on the upper part to secure the lobe in position. Where the securing formation is provided by an opening, the opening may be configured to engage a complementary projection, such as a bolt, arm, pin or tongue, on the upper part. To generate optimal dynamic tension in the flexible tensioning element, the lobe may be oriented in a generally downward pointing direction with respect to the upper part, although other orientations of the lobe may also be used.

The knee brace may further include a calf supporting member, which may be hingedly secured to an operatively lower portion of the lower part, at or about an ankle region thereof, by a pivot member. The calf supporting member may define an elongate channel for receiving and supporting a posterior region of a user's lower leg, which may extend from the user's lower Achilles tendon region to the user's upper calf muscle region. The flexible element may be secured to the calf supporting member to provide dynamic support to the user's calf during knee flexion or pivoting of the upper part relative to the lower part. The flexible tensioning element may be configured to urge the calf supporting member to pivot about the pivot member in an anterior direction when the flexible tensioning element is tensioned, such as during knee flexion. The calf supporting member may be operatively pressed against the posterior region of the user's lower leg as dynamic tension is generated in the flexible tensioning element.

The calf supporting member is preferably manufactured from a light weight, rigid or semi-rigid material, such as a foam polymer or mouldable plastic and may be shaped to provide a custom fit to a specific user.

The knee brace may have a medial side, operatively positioned adjacent the user's inner leg, and a lateral side operatively positioned adjacent the user's outer leg. The medial and lateral sides may be secured together at their upper parts by a rigid thigh support or bridge, which may be shaped to fit over the front of a user's thigh in use. The medial and lateral sides may also be secured together through mutual attachment to the calf supporting member.

The knee brace may include a further lobe such that the two lobes together provide a medial lobe and a lateral lobe respectively. Thus, the knee brace may include a medial lobe, secured adjacent a medial hinge, and a lateral lobe secured adjacent a lateral hinge.

In some embodiments, a common flexible tensioning element may extend between the medial and lateral sides and may be received against a posterior surface of the calf support member by a receiver, such as a hook, loop, or laterally extending sleeve. In other words, a single flexible tensioning element may extend from the upper part of the medial side, to the calf support member, and then to the upper part of the lateral side.

The common flexible tensioning element may engage both the medial and lateral lobes.

The common flexible tensioning element may be adjustable to a desired user tension by activation of a tension modulator located at one or both of the ends of the flexible element.

The flexible tensioning element may have a minimal degree of resilience, preferably no detectable resilience, when stretched to permit a greater transfer of dynamic tension and anterior force into the calf supporting member.

In some embodiments, separate flexible tensioning elements may engage the medial and lateral lobes. The flexible tensioning elements may be independently secured to the upper part at one end and the calf supporting member at an opposite end. Each of the separate flexible tensioning elements may be independently adjustable to a desired user tension by activation of a tension modulator to permit different tensions to be generated on the medial and lateral sides of the knee during flexion, which may be required by some users.

The tension modulator may include one or more of a ratchet (such as a linear, ladder, buckle or dial ratchet) having a gear and pawl mounted on a base, a hook and pile fastener system, a spring loaded tensioner, a strap or a cable, although any suitable tensioning means may be employed. Indicia corresponding to different levels of tension in the flexible element may be provided with the tension modulator to guide a user in selecting a desired level of tension.

Strapping may be provided for securing the upper part about the user's thigh and the lower part about the user's shin. The strapping may include padding, which may be made from breathable material, and a securing means, such as a buckle, hook and pile fastener, clip, button, or the like. The strapping may operatively form a circumferential loop about a user's thigh and/or lower leg.

The knee brace is fitted onto a user's leg by opening the strapping and sliding the brace over the user's leg until the thigh support is positioned over the front of the user's thigh, the user's calf is located in the calf supporting member, and the hinge is located adjacent the user's knee. The strapping is secured about the user's thigh and lower leg, respectively, and tension in the flexible tensioning element adjusted to a desired level by operation of the tensioning modulator. The user can then operate the braced leg in a relatively normal manner.

Figure 2:
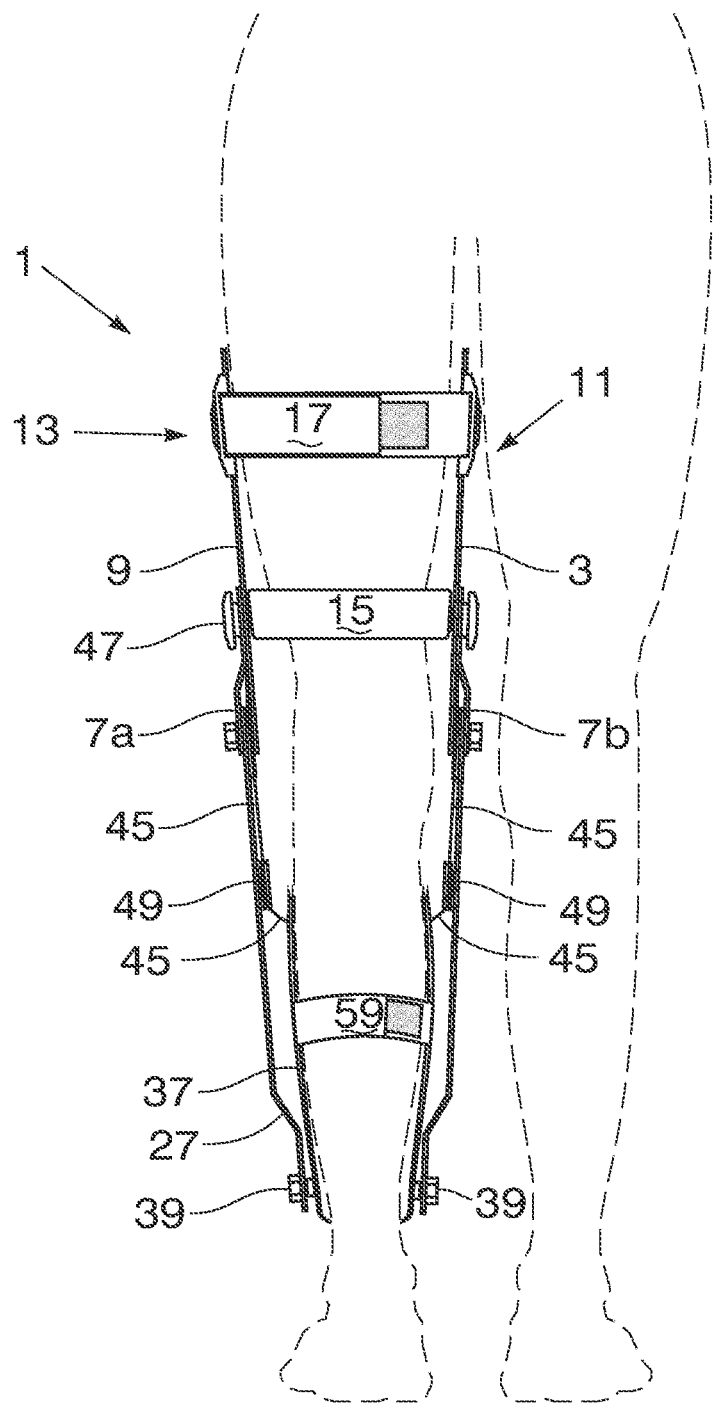
FIG. 2 is a front view of the knee brace of FIG. 1 installed on a user's leg.
Figure 3:
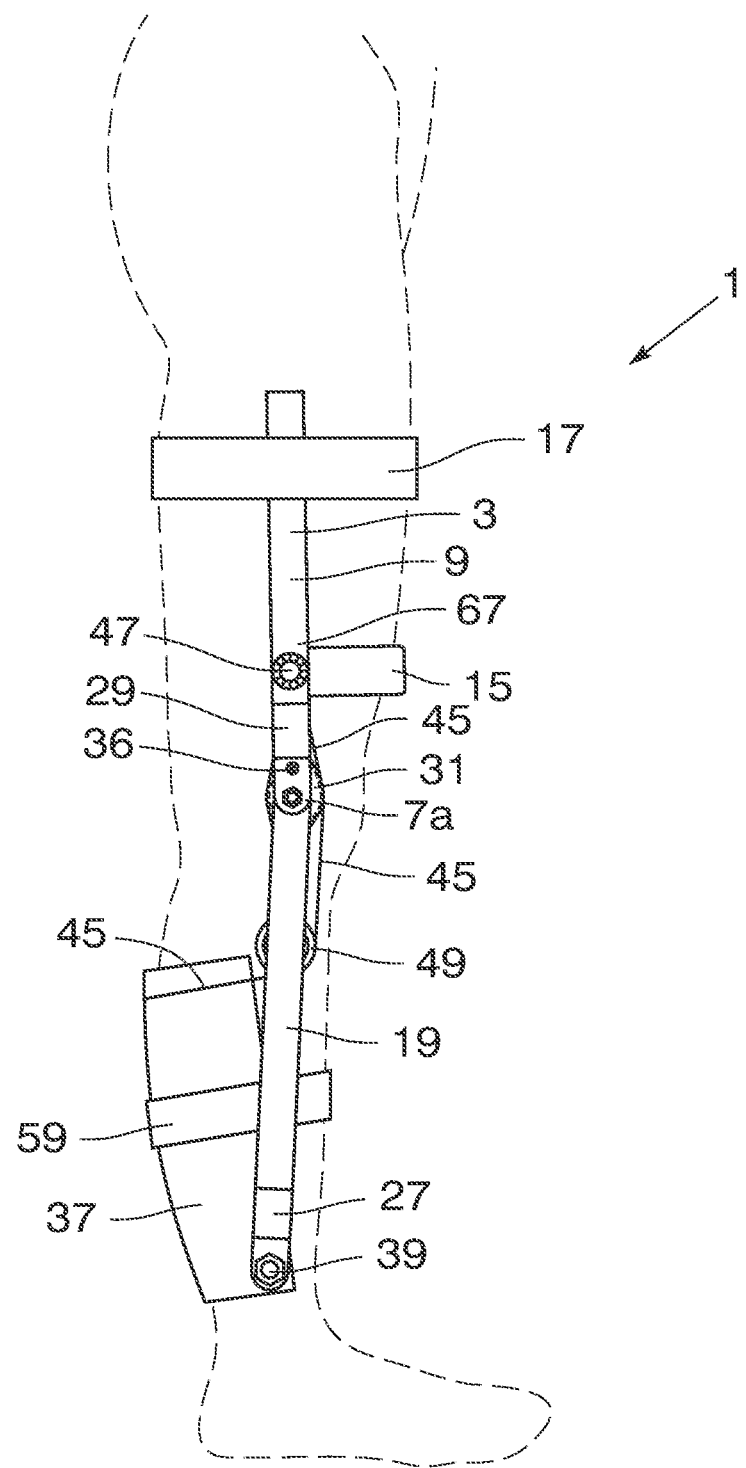
FIG. 3 is a side view of the knee brace of FIG. 1 installed on a user's leg.
Figure 4:
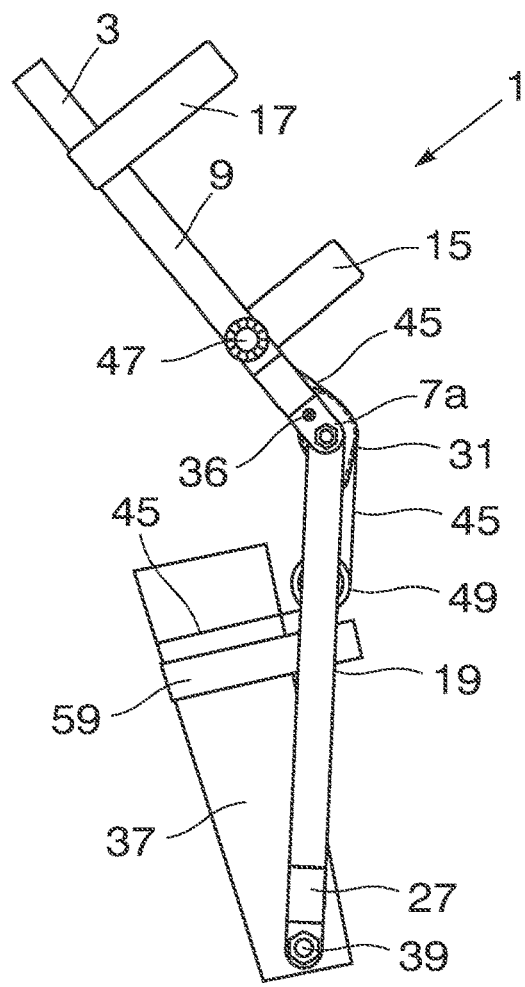
FIG. 4 is a side view of the knee brace of FIG. 1 showing the upper part pivoted relative to the lower part.

In one embodiment of the knee brace, as shown in FIGS. 1 to 7, a knee brace (1) includes an upper part (3) and a lower part (5) secured together by a lateral hinge (7a) and a medial hinge (7b). The upper part (3) includes a pair of straight, flat upper struts (9) located opposite each other on medial (11) and lateral (13) sides of the brace (1) in generally parallel orientation to each other. A curved, rigid bridge (15) for holding the medial (11) and lateral (13) sides of the brace fixed relative to each other extends between the upper struts (9) near the hinges (7a, 7b) and is locatable over a user's quadriceps muscles in use. An upper strap member (17) for securing the upper part (3) about a thigh of the user is attached to each of the upper struts (9) by a securing plate (18) near their free ends. Each securing plate (18) is bolted, riveted or glued to the upper struts (9) and includes an eyelet through which the first strap member is received and secured in position. The upper strap member (17) includes padding for comfort and an adjustable fastener, which in the embodiment illustrated in FIGS. 1 to 3, is a hook and pile fastener, which can be adjusted to fit different user thigh sizes. The upper strap member (17) may effectively form a circumferential loop about the thigh of the user in use.

The lower part (5) includes a pair of lower struts (19) located on the medial (11) and lateral (13) sides of the brace (1) which are respectively connected to the upper struts (9) through the lateral hinge (7a) and medial hinge (7b). Each lower strut (19) includes a straight, flat upper section (25) in generally parallel orientation to the other, and an inwardly inclined lower section (27), arranged to accommodate an outer shape or profile of a typical human lower leg. The lateral and medial hinges (7a, 7b) are operatively located adjacent a user's knee on the lateral and medial sides respectively.

Figure 7:
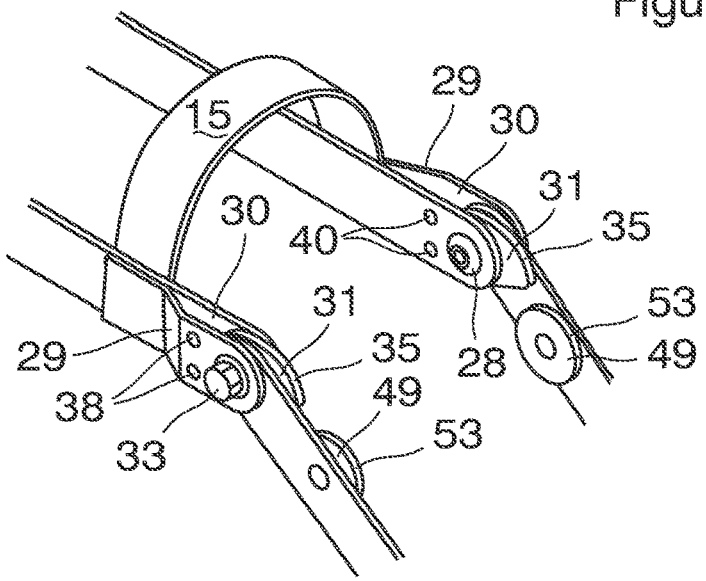
FIG. 7 is a three dimensional view of the hinges and pulley members of the knee brace shown in FIG. 1.

As shown more clearly in FIG. 7, each hinge includes an operatively bottom end of an upper strut (9) and an outwardly stepped tab (29) which together form a bifurcated hinge knuckle (30) that receives an operatively upper end of a lower strut (19) and a lobe (31) between its ends, with the lobe adjacent an inner end of the knuckle. The upper strut (9), stepped tab (29), lower strut (19) and lobe (31) are secured together by a screw threaded first bolt (not shown) extending through each of these components. A washer or bearing may be provided to facilitate smooth movement of the hinge. The first bolt includes a cap (28), as shown in FIGS. 1 and 7, and is secured in place by a first nut (33). Removal of the first nut (33) permits the hinge (7a, 7b) to be disassembled and reassembled with relative ease. This in turn allows the lobe (31) to be replaced with lobes of different configurations, particularly different shapes and sizes, according to the user's requirements.

The lobe (31) is secured in fixed relation to the upper strut (9) firstly by engagement of an aperture (32) in the lobe with the first bolt, and secondly by engagement of an opening (34) in the lobe with a removable pin (36) extending between opposite ends of the bifurcate hinge knuckle (30). The removable pin (36) extends through an outer hole (38) through the opening (34) and into an inner hole (40) in the knuckle. An inner tip of the pin (36) is preferably screw threaded and configured to engage complimentary screw thread in the inner hole (40) so that it may be screwed into position. The pin (36) may alternatively have a flat head at a first end and a tip at an opposite end which is receivable into a removable cap which allows the pin to be introduced into the inner hole (40), guided through the opening (34), and extend through the outer hole (38) where it can be capped in position. The stepped tab (29) includes two outer holes (38) that are co-aligned with two inner holes (40) in the strut (9) to provide different positions in which the lobe (31) can be secured. However, a single hole, or alternatively, multiple holes may also be provided for this purpose.

Figure 5:
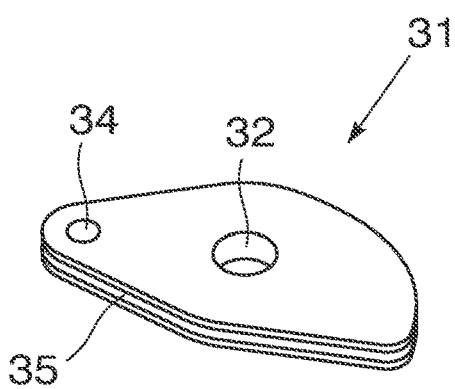
FIG. 5 is a three dimensional view of a lobe forming part of the knee brace.
Figure 6:
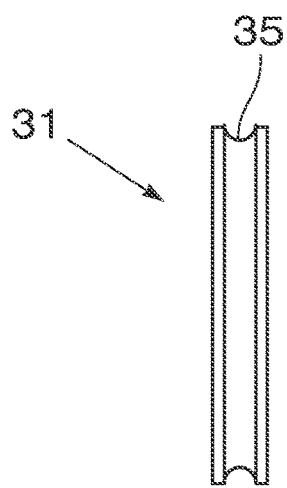
FIG. 6 is a side view of a lobe forming part of the knee brace.

The lobe (31) extends in a generally downward pointing orientation with a curve of the lobe (31) sloping downwards and away from an anterior side of the brace (1). The curve has an involute slope which increases along a perimeter of the curve in the downward direction. As shown in FIGS. 5 and 6, the lobe includes a radiused groove (35) about its periphery for receiving a flexible, elongate tensioning element (45).

Figure 8:
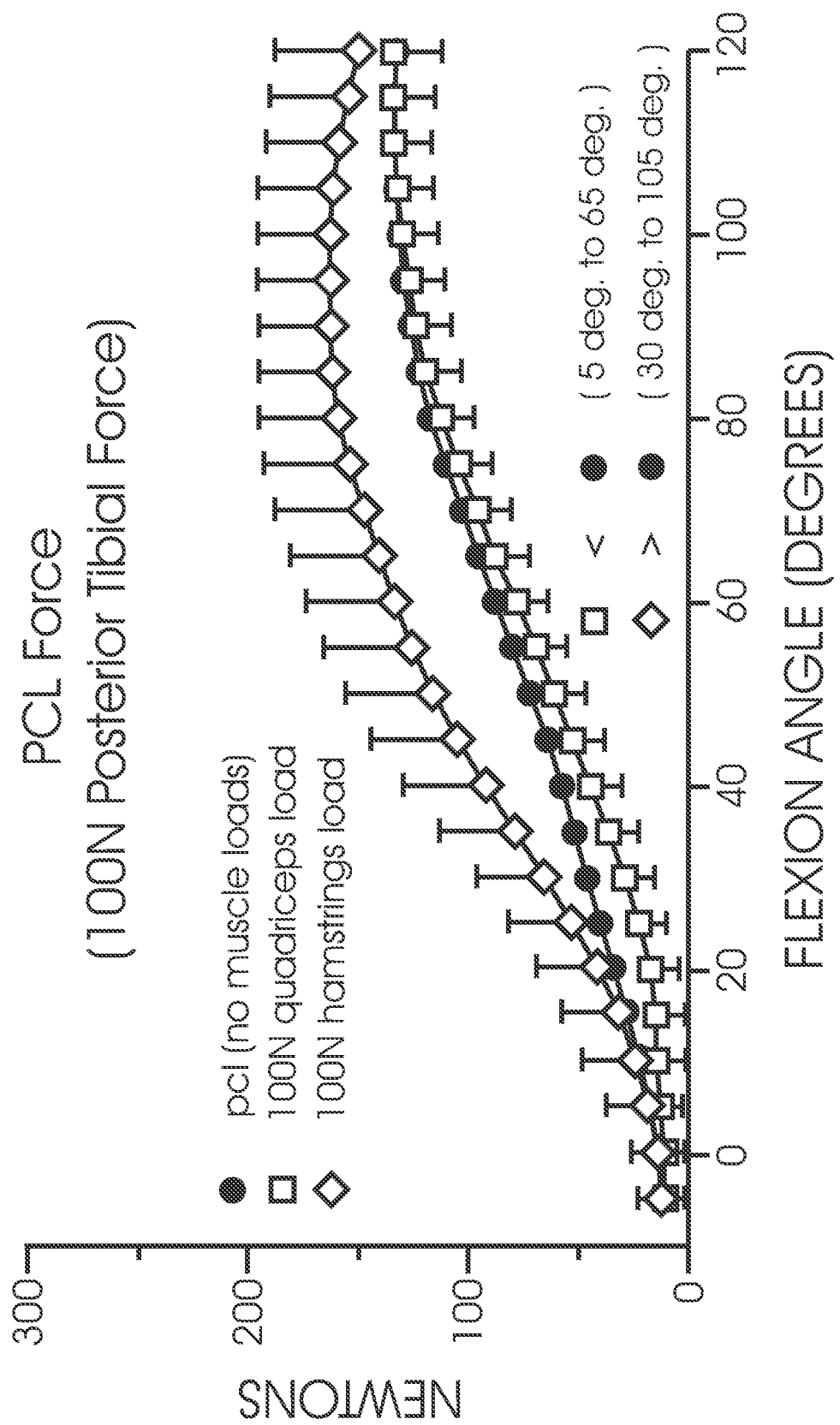
FIG. 8 is a graph illustrating forces acting on a PCL at different degrees of knee flexion.

A periphery of the lobe is shaped to approximate a shape of a force graph (an example of which is illustrated in FIG. 8) corresponding to tensile forces acting on a typical human's PCL at different angles of knee flexion. A perimeter of the lobe can be mapped to data points of the graph, in which each data point corresponds to a degree of flexion and a corresponding force experienced by the PCL. By mapping the data points to the periphery of the lobe, the lobe can be shaped so that an equivalent degree of tension can be generated in the flexible tensioning element at each degree of knee flexion as the flexible tensioning element wraps around the periphery of the lobe during pivoting of the lower part of the brace relative to the upper part.

A generally parabolic curve that approximates the shape of the force graph can be created over a surface of the lobe that is in operative contact with the flexible tensioning element. The surface of the lobe can be manually shaped (for example, by cutting and shaping a suitably sized disc), or by 3D printing the lobe, or by any other suitable means, to visually approximate the shape of the force graph. The parabolic curve may be selected to cause an exponential increase in an anterior force applied to a user's tibia during flexion of the knee brace. The periphery of the lobe is mapped until a 90° flexion point of the knee, whereafter the periphery is assigned a constant radius with respect to the aperture (32) in order to increase the tension at an increasing rate with each further increase in flexion. The mapping function is therefore changed from an exponential dynamic forcing function into a linear function after the 90° point.

The shape of the profile derived from the data points is used as a starting point. Once the initial curvature of the lobe has been created, a further increase is made to the gradient and growth of the curve line so as to apply a greater anterior force to the calf supporting member than would be expected to the experienced by the PCL in an opposite direction during knee flexion. In this way, the knee brace can be configured to prevent any elongation of the PCL resulting from a posterior force.

The configuration of the lobe can be easily customised for different load characteristics resulting from different patient characteristics, such as different knee surface profiles. In some cases, as the tibia translates and rotates about the femur during knee flexion, it may travel along a non-linear path due to differences in the radii of the medial and lateral heads. Should the load profile be required to differ on the medial and lateral heads, the profiles of the lobes on the lateral and medial sides of the brace may be selected to have different curvatures to achieve this.

A calf supporting member (37), in the form of a calf cup in this embodiment, is hingedly secured at its lower end to the operatively lower end of the lower struts (19), proximate an ankle region of the user, by pivot members (39). Each pivot member (39) includes a second bolt (not shown) extending from the calf supporting member (37) through an aperture in the lower end and secured in place by a second nut (41). Washers may be provided to facilitate smooth movement of the pivot members (39). As shown in FIGS. 1 to 4, the calf supporting member (37) defines an elongate channel for receiving and supporting the user's calf region from the user's lower Achilles tendon region to the user's upper calf region.

The curved bridge (15) is secured to each of the struts (9) of the upper part (3) proximate the hinges (7a, 7b). Ends of the bridge are sandwiched between the flat upper strut (9) and a flat section of the outwardly stepped tab (29) that is closest to the strut (9). The strut, bridge and outwardly stepped tab are laminated together, preferably by welding, although they may also be glued, bolted or adjoined by another suitable means. It is not essential that the bridge is secured between the stepped tab and strut and it could equally be secured at any suitable position along the strut. The flat section of the outwardly stepped tab (29) includes an aperture within which a tensioning modulator (47) for adjusting tension in the flexible tensioning element (45) is seated. The aperture and tensioning modulator (47) are preferably located on the lateral side (13) of the brace (1) for ease of access by a user, although they could also be located on the medial side (11) or on both the lateral and medial sides. A groove or channel extends from the aperture to the bifurcate hinge knuckle (30) between the flat section of the stepped tab (29) and the strut (9) through which the flexible tensioning element (45) passes from the tension modulator (47) to an anterior periphery of the lobe (31).

In this embodiment, as shown in FIGS. 1 to 4, the flexible tensioning element (45) is provided by a cable. The cable extends over the radiused groove (35) of the lobe (31) to an anterior periphery of a pulley member (49). As shown in FIGS. 1 and 7, the pulley member (49) includes a circumferential groove (53) within which the cable is slidably received. The pulley member (49) is rotatably secured to an inner surface of the lower struts (19) proximate the lateral and medial hinges (7a, 7b) and in line with the groove (35) of the lobe (31) so that minimal lateral diversion of the cable (45) occurs between the lobe (31) and pulley member (49). The cable (45) extends from the pulley member (49) over a posterior surface (51) of the calf supporting member (37). The cable (45) is received through a small section of cable housing secured about the posterior surface (51) of the calf support member. The cable housing is tubular and extends partway about the posterior surface (51) of the calf support member with the cable slidably received in it. From the posterior surface (51), the cable passes over an anterior periphery of another pulley member located on an inner surface of an opposite strut. The cable passes through a circumferential groove (53) in the pulley member (49) to a circumferential groove (35) located on an anterior periphery of another lobe (31) located on the opposite strut. From the circumferential groove (35) of the lobe, the cable (45) passes either to a fastener, which secures the cable to the strut (9), or to another tensioning modulator (47) located on the strut (9).

In the embodiment illustrated in FIGS. 1 to 7, the tensioning modulator (47) is provided by a dial positioned over a junction between the upper strut (9) and bridge (15), although it could equally be positioned at any suitable position along the strut or along a path defined by the flexible tensioning element (45). The dial of the tensioning modulator (47) includes a ratchet having a gear and pawl mounted on a base to permit tensioning in the flexible tensioning element (45) to be modulated by rotation of the dial. Tension in the flexible tensioning element (45) is increased by rotation of the dial in a first direction and decreased by rotation of the dial in an opposite second direction. As the dial rotates, a "click" can be heard, and preferably also felt, as the pawl slides between adjacent gears to increase or decrease tension.

A lower strap member (59), secured to the lower struts (19) or the calf supporting member is configured to fit about the user's lower leg and hold the lower part (5) in position. The lower strap member (59) is secured in position by a hook and pile fastener, although any suitable securing means (including straps, clips, ratcheting means e.g. a linear, ladder or buckle ratchet, or a combination thereof) that permits adjusting and securing of the second strap member in place may equally be used.

The knee brace (1) can be installed on a user's leg with relative ease. It is fitted by opening the upper and lower strap members (17, 59) and sliding the brace over the user's leg until the bridge (15) is positioned over the front of the user's thigh. The user's calf is then placed in the calf supporting member (37). The first strap member (17) is secured about the user's thigh and the lower strap member (59) about the user's lower leg. The hook and pile fasteners of the first and lower strap members (17, 59) can be adjusted until a snug fit is obtained. The dial of the tensioning modulator (47) can be rotated to achieve a desired level of tension in the flexible tensioning element (45). Once the desired tension has been achieved, the user can operate the braced leg in a relatively normal manner and flex the braced knee when required.

In use, as the user's knee is pulled into flexion, the cable (45) is effectively reduced in length as it wraps around the lobe (31), increasing tension in the cable (45), and correspondingly, increasing an anterior force applied to the calf supporting member (37). The anterior force causes a head of the calf supporting member (37) to remain in constant position with respect to the user's knee, thereby keeping the tibial head located. The calf supporting member (37) is hinged only about the pivot members (39) proximate the user's ankle to ensure that the tibial head is located during flexion of the knee. The length of the calf support member provides a greater degree of support to the lower leg than some knee braces known in the art which only have a strap or small plate extending about a mid-portion of the calf, which ensures that no posterior shifting of the tibia occurs during knee flexion. Furthermore, by hingedly fixing the calf support member to the lower strut, a greater degree of stability is maintained at the knee joint during flexing.

Figure 9:
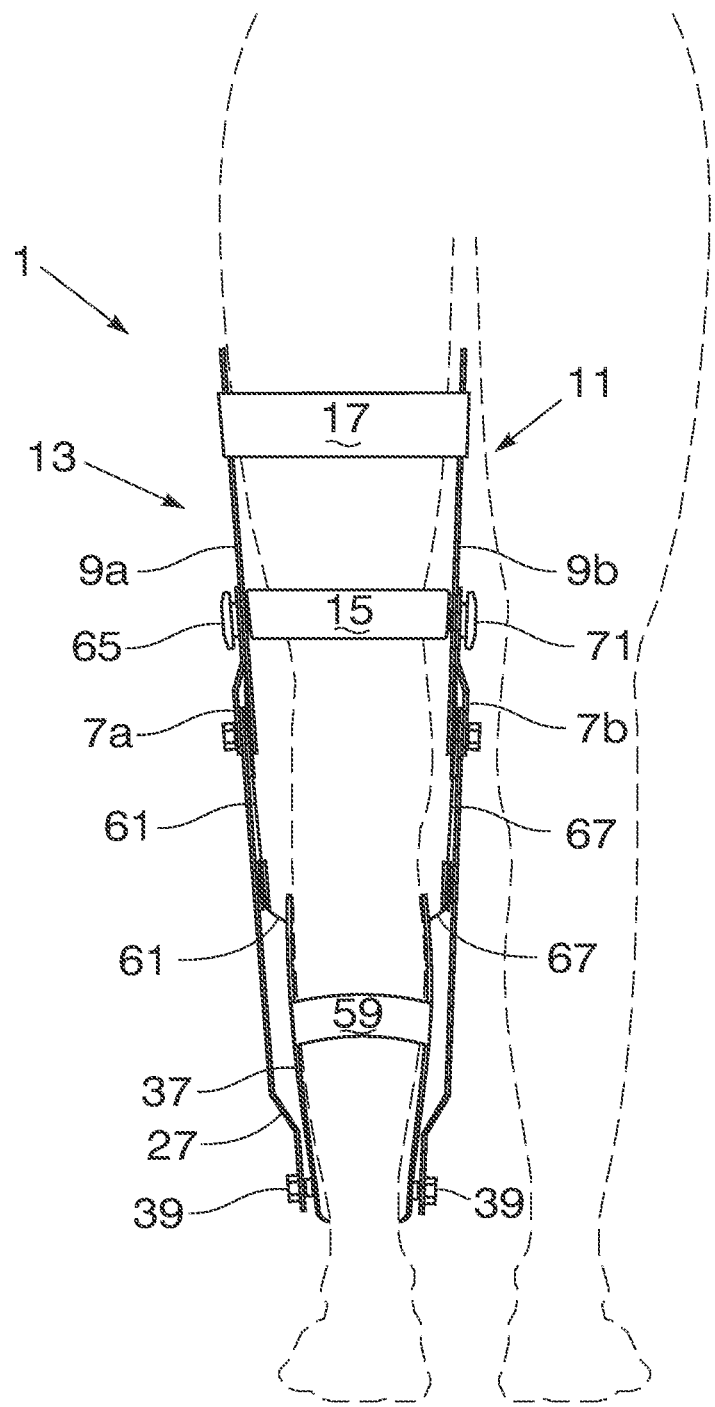
FIG. 9 is a front view of a knee brace according to the present disclosure having two flexible tensioning elements secured about the lateral and medial sides of the brace.
Figure 10:
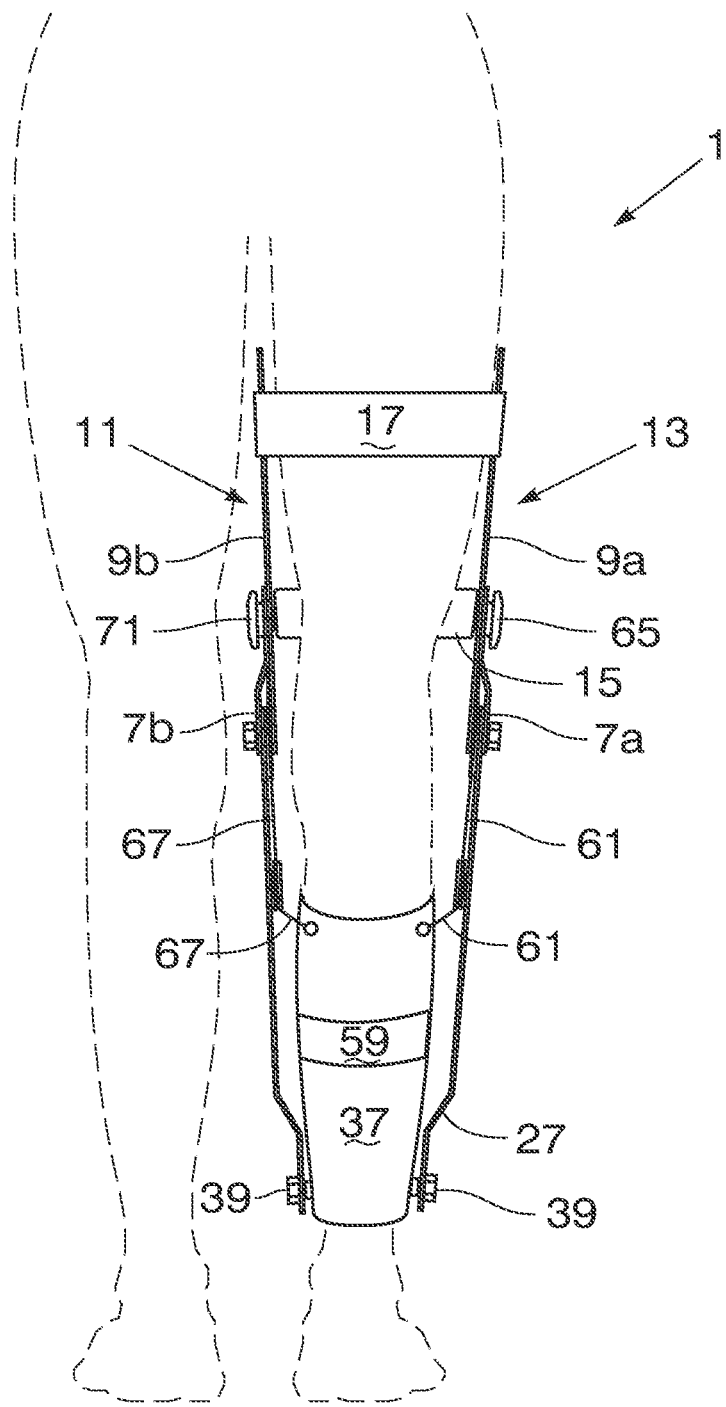
FIG. 10 is a rear view of the knee brace of FIG. 8.
Figure 11:
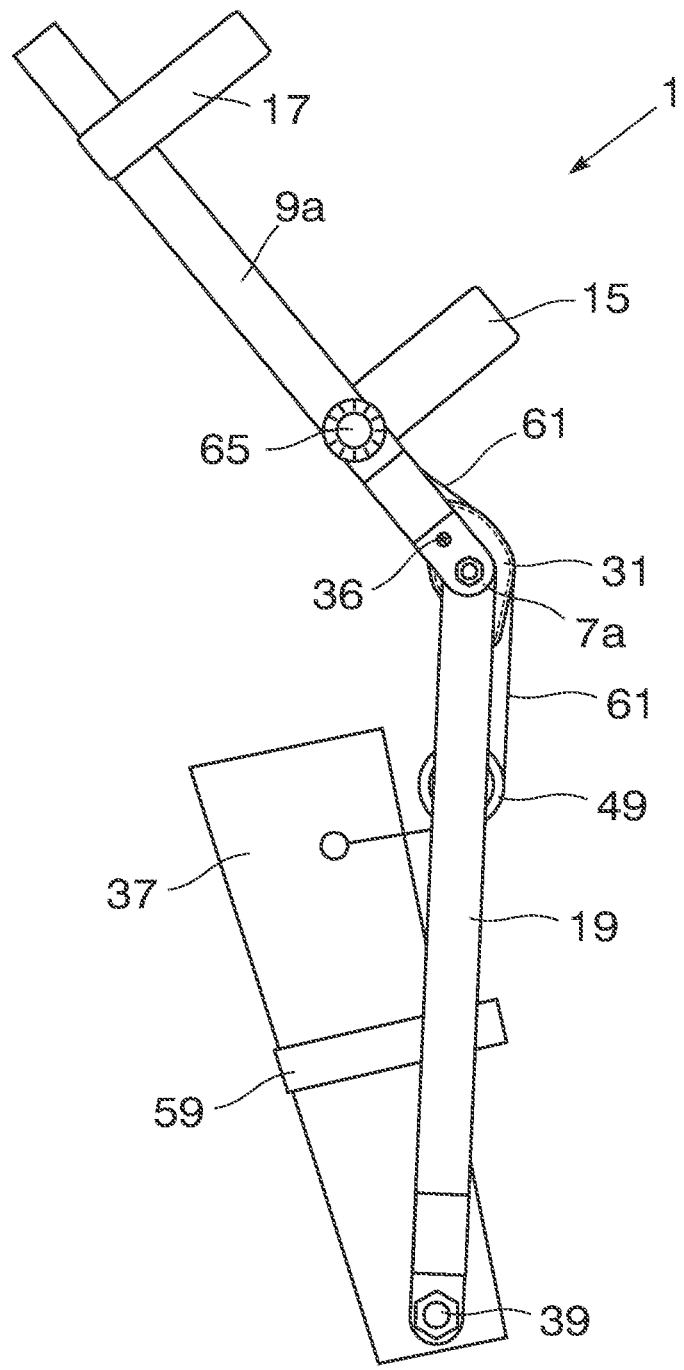
FIG. 11 is a side view of the knee brace of FIG. 9 showing the upper part pivoted relative to the lower part.

Another example embodiment of the knee brace, as shown in FIGS. 9 to 11, has the same configuration except that instead of having a common flexible tensioning element, it includes two separate tensioning elements. A first flexible tensioning element (61) is provided on the lateral side (13) of the device between a first tensioning modulator (65) and the upper lateral side of the calf supporting member (37), and a second flexible tensioning element (67) is provided on the medial side (11) between a second tensioning modulator (71) and the upper medial side of the calf supporting member (37). Each of the first and second flexible tensioning elements (61, 67) is independently adjustable to a desired user tension by way of the tension modulators (65, 71) to permit different tensions to be generated on the lateral (13) and medial (11) sides of the knee brace (1) during flexion. This may be required in circumstances where a patient suffers from combined ligament damage to the knee, requiring specific treatment options. There are often associated injuries combined with a posterior cruciate ligament. The four common scenarios are (1) isolated PCL injury, (2) PCL and posterolateral corner injury, (3) PCL and posteromedial corner injury, and (4) PCL and multiligament injury. Depending on the associated injury it is preferable to have a knee brace that either gives a direct anterior force (isolated PCL), anteromedial force (PCL and posterolateral corner injury), or anterolateral force (PCL and posterolateral corner injury). By being able to change and vary the radius of curvature of the lobe on both sides of the knee, the knee brace allows for different forces to be applied on the different sides and thereby support the injured part of the knee to promote healing.

Figures 12, 13:
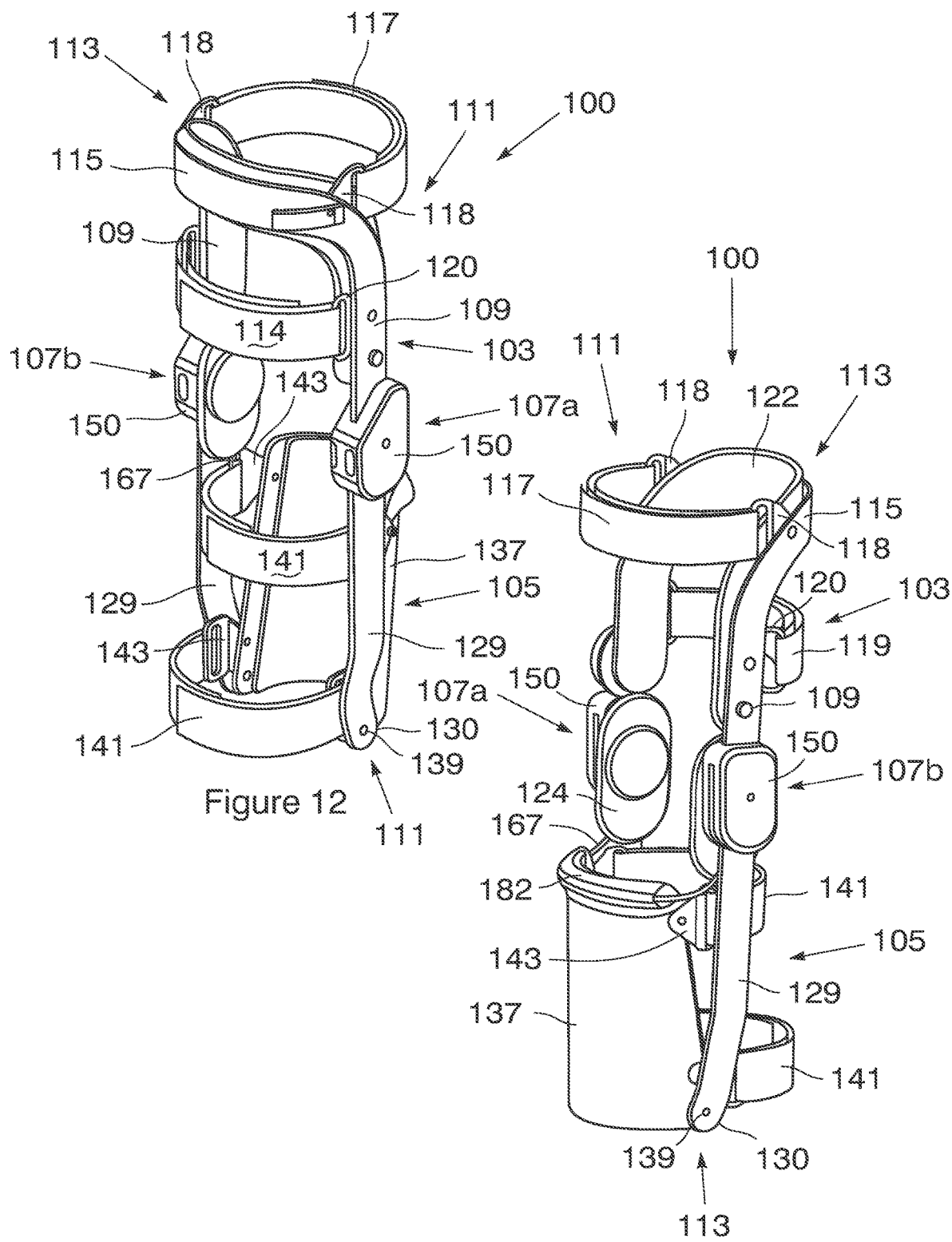
FIG. 12 is a front three dimensional view of a further embodiment of a knee brace.
FIG. 13 is a rear three dimensional view of the knee brace in FIG. 12.
Figure 14:
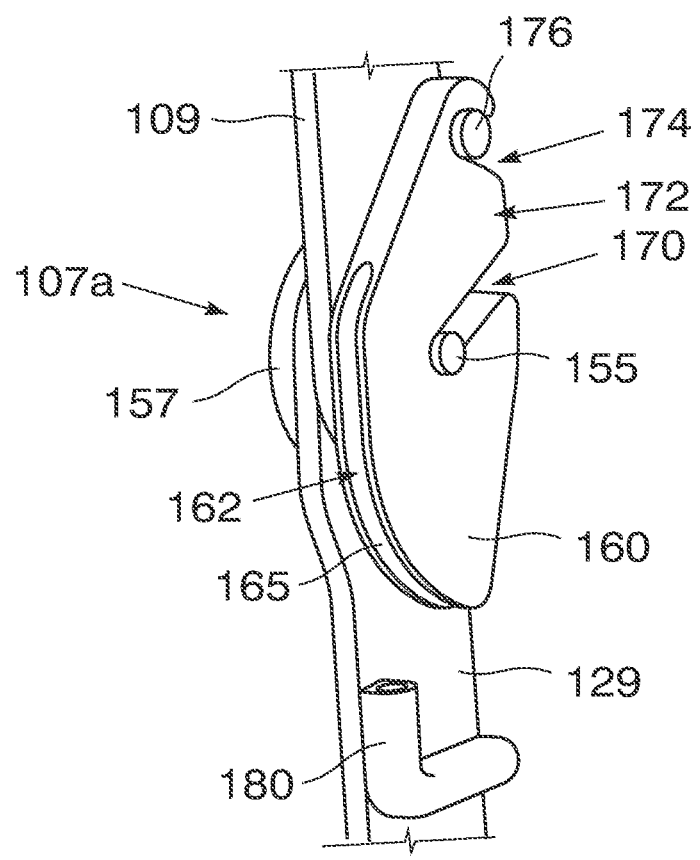
FIG. 14 is a front three dimensional view of the lobe of the knee brace in FIG. 12.

A further example embodiment of a knee brace is shown in FIGS. 12 to 14 and includes an upper part (103) and a lower part (105) secured together by a medial hinge (107a) and a lateral hinge (107b). The upper part (103) has a pair of flat upper struts (109) located opposite each other on medial (111) and lateral (113) sides of the brace (100) in generally parallel orientation to each other with a curved, rigid bridge (115) extending integrally from their respective ends opposite the hinges (107a, 107b). The bridge (115) is thus operatively uppermost and is locatable over a user's quadriceps muscles in use.

A first upper strap member (117) for securing the upper part (103) about a thigh of the user is attached to the bridge (115) by a pair of spaced apart securing plates (118). Each securing plate (118) is, in this embodiment, riveted to the inner surface of the bridge (115) and includes an eyelet through which the first strap member is received and secured in position. The first upper strap member (117) includes an adjustable fastener, in this embodiment a hook and pile fastener, which can be adjusted to fit different user thigh sizes. Together with the bridge (115), the first upper strap member (117) may effectively form a circumferential loop about the thigh of the user in use.

A second upper strap member (119) is similarly secured by plates (120) having suitable eyelets to the upper struts (109) between the bridge (115) and hinges (107a, 107b). The second upper strap member (119) includes an adjustable fastener, in this embodiment also a hook and pile fastener, and extends in the same direction as the bridge (115) to be locatable over the front a user's quadriceps muscles in use.

Padding (122) is provided internally of the upper struts (109) and bridge (115), and further padding (124) is also provided internally of the hinges (107a, 107b).

The lower part (105) includes a pair of lower struts (129) located on the medial (111) and lateral (113) sides of the brace (100) which are respectively connected to the upper struts (109) through the lateral hinge (107a) and medial hinge (107b). The lower struts (129) are generally straight and flat and parallel to each other, with inwardly stepped free ends (130) opposite the hinges (107a, 107b).

A calf supporting member (137), in the form of a calf cup in this embodiment, is hingedly secured at its lower end to the operatively lower end (130) of the lower struts (129). In use, this is proximate an ankle region of the user. Rivets (139) are used in this embodiment to secure the calf cup (137) to the lower struts (109) in a manner that permits rotation of the calf cup (137) with respect to the lower struts (109).

Similarly to the embodiment shown in FIGS. 1 to 4, the calf supporting member (137) defines an elongate channel for receiving and supporting the user's calf region from the user's lower Achilles tendon region to the user's upper calf region.

A pair of lower strap members (141) are secured to the calf cup (137) adjacent its upper and lower end respectively through securing plates (143) having suitable eyelets. The straps (141) are configured to fit about the user's lower leg and hold the calf cup (137), and through it the lower part (105), in position. The lower straps (141) are secured in position by hook and pile fasteners, although any suitable securing means that permits adjusting and securing of the second strap member in place may equally be used, including straps, clips, ratcheting means e.g. a linear, ladder or buckle ratchet, or a combination thereof.

A removal cover (150), on which is secured the padding (124) is provided over each hinge (107a, 107b). As shown more clearly in FIG. 14, the operatively lower end of each upper strut (109) is hingedly secured to the upper end of the respective lower struts (129) by a pin (155) which extends beyond the outer side of the upper strut (109). A flange (157) extends from one end of the pin (155) and is located against the lower strut (129) on the inner side of the hinge (107a, 107b).

The upper end of each lower strut (129) is inwardly stepped at the hinge (107a, 107b) so that the respective upper struts (109) and lower struts (129) extend and pivot in generally the same plane.

A lobe (160) is secured to each hinge (107a, 107b) on the operatively outermost side abutting the upper struts (109) and within the cover (150). A front, or anterior, periphery (162) of the lobe (160) has a generally downward pointing orientation with a curve sloping downwards and away from an anterior side of the brace (100). The curve has an involute slope which increases along a perimeter of the curve in the downward direction and is shaped to approximate a shape of a force graph as described previously. A radiused groove (165) is provided in the front periphery (162) for receiving a flexible, elongate tensioning element (167), in this embodiment a cable.

An operatively downwardly inclined first slot (170), shaped to receive the protruding part of the pin (155), extends inwardly from the rear periphery (172) of the lobe to about its centre. A second, upwardly inclined slot (174) extends inwardly from the rear periphery (172) of the lobe near its operatively upper end and is shaped to receive a lug (176) extending from the upper strut (109) near its posterior side and above the pin (155).

The lobe (160) is secured in place by introducing the pin (155) into the mouth or entrance to the first slot (170) and sliding the lobe (160) over the pin (155) until it abuts the blind end of the slot (170). The lobe (160) is then rotated to locate the lug (176) within the second slot (174). This arrangement allows the lobe (160) to be easily removed or replaced, whilst fixing the lobe (160) relative the upper strut (109) during use and preventing rotating of the lobe (160) during flexion of the brace (100).

A tubular, elbow-shaped guide (180) in which the cable (167) runs is secured to the outer side of the lower strut (129) below the lobe (160) and serves to guide the cable (167) through an approximately 90° turn from contact with the lobe (160) towards the calf cup (137). It serves substantially the same function as the pulley member (49) in the previously described embodiments.

The cable (167) thus extends over the radiused groove (165) of the lobe (160) and through the guide (180) to the uppermost, posterior surface of the calf supporting member (137). Here it runs through a tubular housing (182) in which it is slidably received. The housing (182) extends substantially across the width of the calf cup (137). From the housing (182), the cable (167) passes through the guide (180) on the inner surface of the opposite lower strut (129) to the groove (165) on the anterior periphery (162) of another lobe (160) secured to the opposite upper strut (109).

From the groove (165) of the lobe, the cable (167) passes either to a fastener, which secures the cable to the upper strut (109), or to a tensioning modulator (not shown) located on the strut (109).

As indicated, although the lobes (160) are secured in fixed relation to the respective upper struts (109), they can easily be replaced with lobes of different configurations, particularly different shapes and sizes, according to the user's requirements. Shaping of the lobes (160) and use of the brace will be apparent from the description provided in relation to the previous exemplary embodiments.

By having a reduced number of components, which are all simple to produce and require minimal engineering to assemble, the production costs of the knee brace are relatively low in comparison to some commercially available knee braces. Furthermore, the use of interchangeable lobes and/or separate flexible tensioning elements on the medial and lateral sides, permits different levels of tension to be applied to the medial and lateral sides of the calf support member, which may be necessary for rehabilitation of a knee which flexes in a non-linear orientation or which requires unique tensioning. Interchangeability of the lobes may also allow the knee brace to be adjusted to a specific user's requirements, for example, by generating a higher or lower level of dynamic tension in the flexible tensioning element for heavier or lighter users, respectively. A load profile generated in the flexible tensioning element during flexion can also be adjusted according to a user's preferences, for example, generating a higher or lower rate of tension increase at positions along a flexion pathway, by adjusting a curvature of the lobe which engages the flexible tensioning element. Maintenance and servicing of the knee brace is made relatively easy and inexpensive by the simplicity of the parts and the minimal number of components.

The brace may be useful for all population types, including children and younger persons. The modular construction of the brace makes it easy to adapt to leg size and dynamic tension requires, including those of children and younger persons. Also, the replaceability of the lobes facilitates changing the dynamic tension to suit the user as the user heals or grows. This feature could be particularly useful in children or younger persons who are still growing.

The foregoing description has been presented for the purpose of illustration; it is not intended to be exhaustive or to limit the invention to the precise forms disclosed. Persons skilled in the relevant art can appreciate that many modifications and variations are possible in light of the above disclosure. For example, the hinge could be provided in a variety of different configurations capable of hinging the upper and lower parts relative to each other. The calf supporting member may be free of the lower part and only secured to the flexible tensioning element. In this embodiment, the second strapping member may secure the calf supporting member about a user's calf region, and a third strapping member may be provided for securing the lower part about an ankle region of the user's lower leg. In further embodiments, the lobe may be secured to the upper part above the hinge to urge the flexible tensioning element away from the hinge in an anterior direction. In still further embodiments, the pulley members may be provided by non-rotatable static groove formations configured to receive the flexible tensioning element therein.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A knee brace having an upper part securable about a user's thigh and a lower part securable about the user's lower leg, the upper and lower parts secured together by a hinge, characterized in that an elongate flexible tensioning element extends between the upper part and the lower part over a lobe which is secured to the upper part adjacent to the hinge such that pivoting of the upper part relative to the lower part about the hinge causes tension in the elongate flexible tensioning element and wherein the lobe is shaped to cause the tension to dynamically increase as the upper part is pivoted relative to the lower part, wherein the lobe defines an involute curved surface about its periphery, wherein the knee brace further comprises a calf supporting member, and wherein the elongate flexible tensioning element is secured to the calf supporting member, and wherein the calf supporting member is hingedly secured to an operatively lower portion of the lower part by a pivot member, and the elongate flexible tensioning element is configured to urge the calf supporting member to pivot about the pivot member in an anterior direction.

2. A knee brace as claimed in claim 1, wherein the lobe is releasably secured to the upper part.

3. A knee brace as claimed in claim 2, wherein the lobe includes a securing formation configured to engage a complementary engaging formation on the upper part to secure the lobe in fixed orientation with respect to the upper part.

4. A knee brace as claimed in claim 3, wherein the securing formation is provided by a clip, latch, detent, tongue, groove or opening.

5. A knee brace as claimed in claim 3, wherein the securing formation is provided by an opening configured to engage a complementary projection on the upper part.

6. A knee brace as claimed in claim 2, wherein the lobe is secured so that it does not rotate or move with respect to the upper part during pivoting of the upper part relative to the lower part.

7. A knee brace as claimed in claim 1, including a further lobe such that the lobe and the further lobe together comprise a medial lobe and a lateral lobe and separate elongate flexible tensioning elements engaging the medial and lateral lobes respectively.

8. A knee brace as claimed in claim 7, wherein the separate elongate flexible tensioning elements engaging the medial and lateral lobes are each independently adjustable to a desired user tension.

9. A knee brace as claimed in claim 1, wherein the calf supporting member is configured to support a region of the user's lower leg extending from the user's lower Achilles tendon region to the user's upper calf region.

10. A knee brace as claimed in claim 1, including a further lobe such that the lobe and the further lobe together comprise a medial lobe and a lateral lobe and a common elongate flexible tensioning element engaging both the medial and lateral lobes.

* * * * *